(12) United States Patent  (10) Patent No.: US 7,115,762 B2
Luo  (45) Date of Patent: Oct. 3, 2006

(54) POLYSTYRENE-SUPPORTED PALLADACYCLE CATALYSTS

(75) Inventor: Fen-Tair Luo, Taipei (TW)

(73) Assignee: Academia Sinica, Taipei (TW)

( * ) Notice: Subject to any disclaimer, the term of this patent is extended or adjusted under 35 U.S.C. 154(b) by 55 days.

(21) Appl. No.: 10/884,844

(22) Filed: Jul. 2, 2004

(65) Prior Publication Data

US 2006/0004216 A1  Jan. 5, 2006

(51) Int. Cl.
*C07F 15/00* (2006.01)
*B01J 31/00* (2006.01)
*C07C 253/00* (2006.01)

(52) U.S. Cl. .................. 556/20; 556/136; 502/159; 568/314; 568/316; 560/8

(58) Field of Classification Search ............. 556/20, 556/136; 502/159; 568/314, 316; 560/8
See application file for complete search history.

(56) References Cited

U.S. PATENT DOCUMENTS 5,831,107 A * 11/1998 Beller et al. .............. 556/16
5,886,240 A *  3/1999 Beller et al. ............. 568/797
6,084,114 A *  7/2000 Geissler et al. ........... 556/21

OTHER PUBLICATIONS

Parrinello et al., Platinum-Catalyzed Asymmetric Hydroformylation with a Polymer-Attached Aptically Active Phosphine Ligand, Journal of Organic Chemistry, 1986, vol. 51, No. 22, pp. 4189-4195.*
Benvenuti et al., "Hydrogenation of Organic Substrates by an heterogenized catalyst based on a bis(diphenylphosphino)methane polymer-bound palladium(II) complex", Journal of Molecular Catalysis A: Chemical, 145: 221-228, 1999.
Bergbreiter et al., "Tridentate SCS Palladium(II) Complexes: New, Highly Stable, Recyclable Catalysts for the Heck Reaction", J. Am. Chem. Soc., 121:9531-9538, 1999.
Bergbreiter et al., "Thermomorphic Rhodium(I) and Palladium(0) Catalysts", J. Am. Chem. Soc., 120:4250-4251, 1998.
Bergbreiter et al., "Palladium-Catalyzed C-C Coupling under Thermomorphic Conditions", J. Am. Chem. Soc., 122:9058-9064, 2000.
Herrmann et al., "Heck reaction catalyzed by phospha-palladacycles in non-aqueous ionic liquids", Journal of Organometallic Chemistry, 572:141-145, 1999.
Inada et al., "The Cross-Coupling Reaction of Arylboronic Acids with Chloropyridines and Electron-Deficient Chloroarenes Catalyzed by a Polymer-Bound Palladium Complex", Tetrahedron, 56:8661-8664, 2000.
Nowotny et al., "Cyclopalladated imine catalysts in Heck arylation: search for the catalytic species", Chem. Commun., 1877-1878, 2000.
Su-Bum Jang, "Polymer-bound Palladioum-catalyzed Coupling of Allylic Alcohols with Hypervalent Iodonium Salts" Tetrahedron Letters, vol. 38, No. 25, pp. 4421-4424, 1997.
Su-Bum Jang, "Polymer-bound Palladium-catalyzed Cross-coupling of Organoboron Compounds with Organic Halides and Organic Triflates", Tetrahedron Letters, vol. 38, No. 10, pp. 1793-1796, 1997.
McNamara et al., "Recoverable Catalysts and Reagents Using Recyclable Polystyrene-Based Supports", Chem. Rev. 102:3275-3300, 2002.
Parrish et al., "Use of Polymer-supported Dialkylphosphinobiphenyl Ligands for Palladium-Catalyzed Amination and Suzuki Reactions", J. Org. Chem., 66:3820-3827, 2001.

(Continued)

*Primary Examiner*—Porfirio Nazario-Gonzalez
(74) *Attorney, Agent, or Firm*—Fish & Richardson P.C.

(57) ABSTRACT

This invention relates to a recyclable palladacycle catalyst of formula

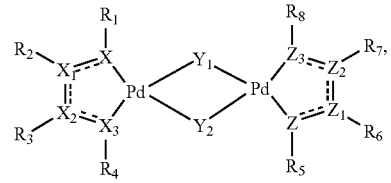

in which each ═══ is a single bond or a double bond, provided that if one ═══ is a double bond, its neighboring ═══ is not a double bond; each of X and Z, independently, is —P(R')—, —S—, —N(R')—, or —N═, in which R' is alkyl, aryl, cyclyl, heteroaryl, or heterocyclyl; each of $Y_1$ and $Y_2$, independently, is an anion of an organic or inorganic acid; each of $X_1$, $X_2$, $X_3$, $Z_1$, $Z_2$, and $Z_3$, independently, is —C═, —CR"—, in which R" is H, alkyl, aryl, cyclyl, heteroaryl, or heterocyclyl; and each of $R_1$, $R_2$, $R_3$, $R_4$, $R_5$, $R_6$, $R_7$, and $R_8$, independently, is H, alkyl, aryl, cyclyl, heteroaryl, or heterocyclyl, or $R_1$, X, $X_1$, and $R_2$, together form a 3–8 membered ring, or $R_2$, $X_1$, $X_2$, and $R_3$, together form a 3–8 membered ring, or $R_3$, $X_2$, $X_3$, and $R_4$, together form a 3–8 membered ring, or $R_5$, Z, $Z_1$, and $R_6$, together form a 3–8 membered ring, or $R_6$, $Z_1$, $Z_2$, and $R_7$, together form a 3–8 membered ring, or $R_7$, $Z_2$, $Z_3$, and $R_8$, together form a 3–8 membered ring; provided that one of $R_1$, $R_2$, $R_3$, $R_4$, $R_5$, $R_6$, $R_7$, and $R_8$, or the ring formed from $R_1$, X, $X_1$, and $R_2$, or the ring formed from $R_2$, $X_1$, $X_2$, and $R_3$, or the ring formed from $R_3$, $X_2$, $X_3$, and $R_4$, or the ring formed from $R_5$, Z, $Z_1$, and $R_6$, or the ring formed from $R_1$, $Z_1$, $Z_2$, and $R_7$, or the ring formed from $R_7$, $Z_2$, $Z_3$, and $R_8$ is connected to a first polymer.

Also included in this invention are a method of promoting a coupling reaction using the above-described palladacycle compound and a method of making it.

35 Claims, No Drawings

OTHER PUBLICATIONS

Rocaboy et al., "Highly Active Thermomorphic Fluorous Palladacycle Catalyst Precursors for the Heck Reaction; Evidence for a Palladium Nanoparticle Pathway", Organic Letters, vol. 4, No. 12, 1993-1996, 2002.

Villemin et al., "Palladium Homogenous and Supported Catalysis: Synthesis of Functional Acetylenics and Cyclisation to Heterocycles", Heterocycles, vol. 29, No. 7, pp. 1255-1261, 1989.

* cited by examiner

POLYSTYRENE-SUPPORTED PALLADACYCLE CATALYSTS

BACKGROUND

Palladacycle is a cyclic compound having a palladium atom as a ring member. Palladacycle compounds, containing one or more heteroatoms, such as phosphorous, nitrogen, and sulfur, have been currently developed and used as catalysts to promote coupling reactions (e.g., the Heck reaction, the Suzuki reaction, and the Sonogashira reaction). Dupont, J., et al. *Eur. J. Inorg. Chem.* 2001, 15, 1917–1927; Herrmann, W. A., et al. *Angew. Chem. Int. Ed. Engl.* 1995, 34, 1844–1848; Beller, M., et al. *Angew. Chem. Int. Ed. Engl.* 1995, 34, 1848–1849; Herrmann, W. A., et al. *J. Mol. Catal. A.* 1996, 108, 51–56; Herrmann, W. A., et al. *J. Organomet. Chem.* 1999, 576, 23–41; and Reetz, M. T., et al. *Angew. Chem. Int. Ed. Engl.* 1998, 37, 481–483.

More recently, particular attention has been drawn to palladacycle catalysts that can be isolated from reaction mixtures and reused. Bergbreiter, D. E., et al. *J. Am. Chem. Soc.* 2000, 122, 9058–9064; Bergbreiter, D. E., et al. *J. Am. Chem. Soc.* 1998, 120, 4250–4251; Bergbreiter, D. E., et al. *J. Am. Chem. Soc.* 1999, 121, 9531–9538; Bergbreiter, D. E. *Catal. Today* 1998, 42, 389–397; and Nowotny, M., et al. *Chem. Commun.* 2000, 1877–1878. However, recyclable catalysts reported so far are not satisfactory. For example, they have low efficacy.

SUMMARY

This invention is based on a surprising discovery of a recyclable polystyrene-supported palladacycle catalyst that has high efficacy in promoting coupling reactions.

One feature of this invention relates to palladacycle catalysts of formula (I)

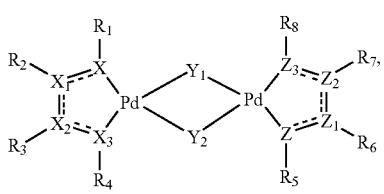

(I)

in which each ==== is a single bond or a double bond, provided that if one ==== is a double bond, its neighboring ==== is not a double bond; each of X and Z, independently, is —P(R')—, —S—, —N(R')—, or —N=, in which R' is alkyl aryl, cyclyl, heteroaryl, or heterocyclyl; each of $Y_1$ and $Y_2$, independently, is an anion of an organic or inorganic acid; each of $X_1$, $X_2$, $X_3$, $Z_1$, $Z_2$, and $Z_3$, independently, is —C=, —CR"—, in which R" is H, alkyl, aryl, cyclyl, heteroaryl, or heterocyclyl; and each of $R_1$, $R_2$, $R_3$, $R_4$, $R_5$, $R_6$, $R_7$, and $R_8$, independently, is H, alkyl, aryl, cyclyl, heteroaryl, or heterocyclyl, or $R_1$, X, $X_1$, and $R_2$, together form a 3–8 membered ring, or $R_2$, $X_1$, $X_2$, and $R_3$, together form a 3–8 membered ring, or $R_3$, $X_2$, $X_3$, and $R_4$, together form a 3–8 membered ring, or $R_5$, Z, $Z_1$, and $R_6$, together form a 3–8 membered ring, or $R_6$, $Z_1$, $Z_2$, and $R_7$, together form a 3–8 membered ring, or $R_7$, $Z_2$, $Z_3$, and $R_8$, together form a 3–8 membered ring; provided that one of $R_1$, $R_2$, $R_3$, $R_4$, $R_5$, $R_6$, $R_7$, and $R_8$, or the ring formed from $R_1$, X, $X_1$, and $R_2$, or the ring formed from $R_2$, $X_1$, $X_2$, and $R_3$, or the ring formed from $R_3$, $X_2$, $X_3$, and $R_4$, or the ring formed from $R_5$, Z, $Z_1$, and $R_6$, or the ring formed from $R_6$, $Z_1$, $Z_2$, and $R_7$, or the ring formed from $R_7$, $Z_2$, $Z_3$, and $R_8$ is connected to a polymer. One or more additional polymers can be connected to at least one of the just-mentioned groups.

One subset of the above-described catalysts feature that each of X and Z is —P(R')—, each of $X_1$ and $Z_1$ is —C=, each of $X_2$ and $Z_2$ is —C=, each of $X_3$ and $Z_3$ is —CR"—, each of the bonds between X and $X_1$, between $X_2$ and $X_3$, between Z and $Z_1$, and between $Z_2$ and $Z_3$ is a single bond, each of the bonds between $X_1$ and $X_2$ and between $Z_1$ and $Z_2$ is a double bond, $R_2$, $X_1$, $X_2$, and $R_3$ together form phenyl, and $R_6$, $Z_1$, $Z_2$, and $R_7$ together form phenyl. In some of these compounds, a polymer is connected to the phenyl formed from $R_2$, $X_1$, $X_2$, and $R_3$ by a covalent bond and another polymer is connected to phenyl formed from $R_6$, $Z_1$, $Z_2$, and $R_7$ by a covalent bond. Each polymer can be a polystyrene. Preferably, the polystyrene has a degree of polymerization of 5, 6, or 7.

An example of the compounds of this invention is shown below:

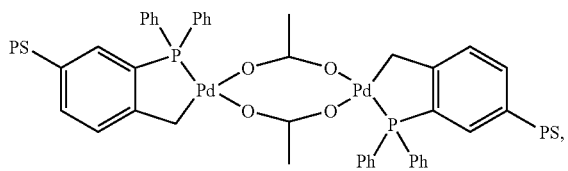

in which PS is styrene having a degree of polymerization of 6.

Another aspect of this invention relates to a method of promoting a coupling reaction by conducting the coupling reaction in the presence of one or more of the palladacycle catalysts of this invention. The coupling reaction can be the Heck reaction, the Suzuki reaction, the Sonogashira reaction, the Stille reaction, the Grignard reaction, Negashi reaction, or the Buchwald-Hartwig amination reaction.

Still another aspect of this invention relates to a method of making the palladacycle catalysts described above. The method includes reacting styrene with a compound of formula (I), in which each ==== is a single bond or a double bond, provided that if one ==== is a double bond, its neighboring ==== is not a double bond; each of X and Z, independently, is —P(R')—, —S—, —N(R')—, or —N=, in which R' is alkyl, aryl, cyclyl, heteroaryl, or heterocyclyl; each of $Y_1$ and $Y_2$ is an anion of an organic or inorganic acid; each of $X_1$, $X_2$, $X_3$, $Z_1$, $Z_2$, and $Z_3$, independently, is —C=, —CR"—, in which R" is H, alkyl, aryl, cyclyl, heteroaryl, or heterocyclyl; and each of $R_1$, $R_2$, $R_3$, $R_4$, $R_5$, $R_6$, $R_7$, and $R_8$, independently, is H, alkyl, aryl, cyclyl, heteroaryl, or heterocyclyl, or X, $R_1$, $R_2$, and $X_1$ together form a 3–8 membered ring, or $X_1$, $R_2$, $R_3$, and $X_2$ together form a 3–8 membered ring, or $X_2$, $R_3$, $R_4$, and $X_3$ together form a 3–8 membered ring, or Z, $R_5$, $R_6$, and $Z_1$ together form a 3–8 membered ring, or $Z_1$, $R_6$, $R_7$, and $Z_2$ together form a 3–8 membered ring, or $Z_2$, $R_7$, $R_8$, and $Z_3$ together form a 3–8 membered ring; provided that one of $R_1$, $R_2$, $R_3$, $R_4$, $R_5$, $R_6$, $R_7$, and $R_8$, or the ring formed from $R_1$, X, $X_1$, and $R_2$, or the ring formed from $R_2$, $X_1$, $X_2$, and $R_3$, or the ring formed from $R_3$, $X_2$, $X_3$, and $R_4$, or the ring formed from $R_5$, Z, $Z_1$, and $R_6$, or the ring formed from $R_6$, $Z_1$, $Z_2$, and $R_7$, or the ring formed from $R_7$, $Z_2$, $Z_3$, and $R_8$ is connected to a vinyl group. One or more additional vinyl groups can be connected to the just-mentioned groups.

One subset of the catalysts prepared by the above method feature that they each have two polystyrene moieties, which are each connected to one of $R_1$, $R_2$, $R_3$, $R_4$, $R_5$, $R_6$, $R_7$, and $R_8$, or the ring formed from X, $R_1$, $R_2$, and $X_1$, or the ring formed from $X_1$, $R_2$, $R_3$, and $X_2$, or the ring formed from $X_2$, $R_3$, $R_4$, and $X_3$, or the ring formed from Z, $R_5$, $R_6$, and $Z_1$, or the ring formed from $Z_1$, $R_6$, $R_7$, and $Z_2$, or the ring formed from $Z_2$, $R_7$, $R_8$, and $Z_3$. This catalyst is prepared from a corresponding compound that has two vinyl groups instead of two polystyrene moieties.

The term "alkyl" refers to a straight or branched hydrocarbon, containing 1–10 carbon atoms. Examples of alkyl groups include, but are not limited to, methyl, ethyl, n-propyl, i-propyl, n-butyl, i-butyl, and t-butyl.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "cyclyl" refers to a saturated and partially unsaturated cyclic hydrocarbon group having 3 to 12 carbons, preferably 3 to 8 carbons, and more preferably 3 to 6 carbons, wherein the cyclyl group may be optionally substituted. Examples of cyclyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5–8 membered monocyclic, 8–12 membered bicyclic, or 11–14 membered tricyclic ring system having 1–3 heteroatoms if monocyclic, 1–6 heteroatoms if bicyclic, or 1–9 heteroatoms if tricyclic, said heteroatoms selected from O, N, or S (e.g., carbon atoms and 1–3, 1–6, or 1–9 heteroatoms of N, O, or S if monocyclic, bicyclic, or tricyclic, respectively), wherein each ring may have 1 to 4 substituents. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5–8 membered monocyclic, 8–12 membered bicyclic, or 11–14 membered tricyclic ring system having 1–3 heteroatoms if monocyclic, 1–6 heteroatoms if bicyclic, or 1–9 heteroatoms if tricyclic, said heteroatoms selected from O, N, or S (e.g., carbon atoms and 1–3, 1–6, or 1–9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

Alkyl, aryl, cyclyl, heteroaryl, and heterocyclyl mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, and heterocyclyl, in which the alkyl, alkenyl, alkynyl, alkyloxy, aryl, heteroaryl, cyclyl, and heterocyclyl may be further substituted.

The term "an anion of an organic acid or inorganic acid" refers to the negatively charged moiety in the molecule of an organic acid or inorganic acid. Examples include, but are not limited to, $HCO_2^-$, $CH_3CO_2^-$, $CF_3CO_2^-$, $CH_3CH_2CO_2^-$, $PhCO_2^-$, $F^-$, $Cl^-$, $Br^{31}$, $I^-$, or $NO_3^-$.

The palladacycle catalysts of this invention may further contain one or more non-aromatic double bonds and one or more asymmetric centers. Thus, they occur as racemates and racemic mixtures, single enantiomers, individual diastereomers, diastereomeric mixtures, or cis- or trans-isomeric forms. All such isomeric forms are contemplated.

The details of one or more embodiments of the invention are set forth in the accompanying drawings and the description below. Other features, objects, and advantages of the invention will be apparent from the description and drawings, and from the claims.

DETAILED DESCRIPTION

The palladacycle catalysts of the present invention can be used to promote a coupling reaction in organic synthesis, e.g., increasing the reaction rate, improving the reaction yield, or lowering the reaction threshold temperature. Thus, within the scope of this invention is a method of promoting a coupling reaction by conducting the reaction in the presence of one or more of the palladacycle catalysts. The term "coupling reaction" refers to a chemical reaction in which two or more molecules or two moieties of a molecule are coupled to each other by a covalent bond, such as a C—C bond, a C=C bond, a C—C bond, a C—N bond, and a C—O bond. Coupling reactions have been well known in the art (see, e.g., F. Diederich and P. J. Stang Ed. *Metal catalyzed Cross-coupling reactions*, Wiley-VCH (1998)). Examples include, but are not limited to, the Heck reaction, the Suzuki reaction, the Sonogashira reaction, the Stille reaction, the Grignard reaction, the Negashi reaction, and the Buchwald-Hartwig amination reaction.

To practice this method, one can mix reactants required in a coupling reaction with a palladium catalyst (or more than one catalyst) of this invention. The reactants may be in a solid state, a liquid state, or a gas state. A solvent, including a solvent mixture, may be used in the reaction. Suitable solvents include, but are not limited to tetrahydrofuran, N,N-dimethylaniline, N,N-dimethylformaide, dimethylsulfoxide, and chloroform. The catalyst, the reactants, and the solvent, if any, can be added in an alternate sequence. For example, the reactants and the solvent are first added to a reaction container and then the catalyst is added. As another example, the catalyst and the solvent are first added to a reaction container, and then the reactants are added.

A coupling reaction may be conducted in the presence of a catalyst of this invention under various conditions. For example, cooling, heating, or refluxing the reaction mixture may be required. As another example, addition of a certain amount of an acid or a base may be required to modify the acidity of the reaction mixture.

The completion of a coupling reaction can be monitored by any method well known in the art, e.g., ultra-violent spectrum, infrared spectrum, nuclear magnetic resonance, thin layer chromatography, gas chromatography, and high performance liquid chromatography.

After the reaction is complete, the product (or products) or the catalyst can be separated from the reaction mixture by one or more conventional separation methods well known in the art, such as chromatography, recrystalation, and distillation. A preferred method to isolate the catalyst is: (1) adding a solution, in which the catalyst has poor solubility, to precipitate the catalyst out, and (2) collecting the precipitated catalyst by filtration. Suitable solvents include, but are not limited to, methanol, ethanol, propanol, actonitride, and acetone. The collected catalyst, with or without further purification, can be used in a coupling reaction again.

Also included in this invention is a method of making the above-described palladacycle catalysts. The method essentially includes reacting a palladacycle compound, which contains one or more double bonds (preferably terminal double bonds), with a monomer to afford a polypolymer-supported paladacycle catalyst. This reaction may be facilitated by heating, radiation, or addition of an initializer.

Shown below is an example in which styrene reacts with a palladacycle compound having two vinyl groups to form a polystyrene-supported palladacycle catalyst:

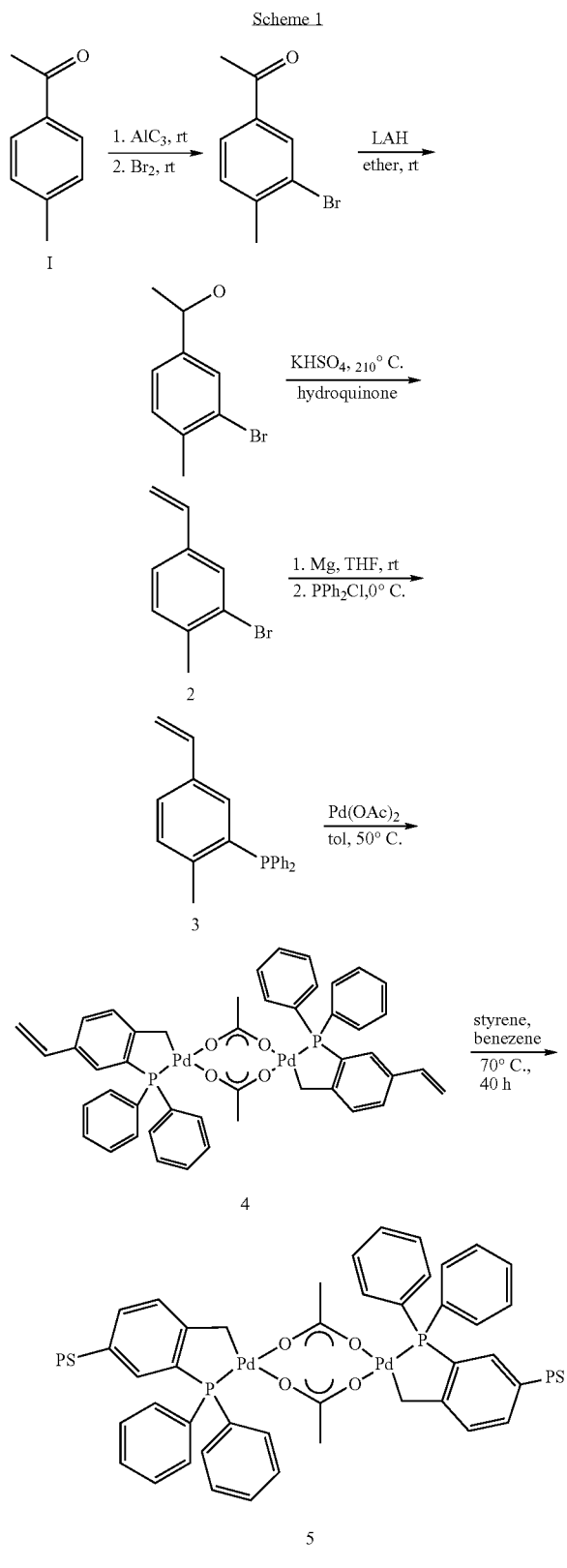

In Scheme 1, 1-bromo-2-methyl-5-vinylphenyl (compound 2) is prepared from 1-acetyl-4-methylphenyl (compound 1) via bromination, reduction, and elimination reactions. Subsequently, compound 2 is coupled with chlorodiphenylphosphine to produce compound 3. Compound 3 is then reacted with palladium acetate to form palladacycle compound 4, which contains two vinyl groups. The two vinyl groups then react with styrene to afford polystyrene-supported palladacycle catalyst 5.

The palladacycle catalysts of this invention can also be prepared by other methods well known in the art. For example, a palladacycle compound having one more functional groups is first prepared. Then, it is coupled with one or more polymers having functional groups reactive to the functional groups of the palladacycle compound to form a palladacyle catalyst of this invention. As another example, a palladacycle salt (e.g., palladium actate) reacts with ligands having one or more polymers to form a palladacycle catalyst of this invention.

The above-described methods for making the palladacycle catalysts may also additionally include steps, either before or after the steps described specifically herein, of adding or removing suitable protecting groups. In addition, various synthetic steps may be performed in an alternate sequence to give the desired catalysts. Synthetic chemistry transformations and protecting group methodologies (protection and deprotection) useful in synthesizing applicable palladacycle catalysts are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Synthesis of Compound 5

(1) Synthesis of 3-bromo-4-methylacetophenone

Anhydrous aluminum chloride (30 g, 225 mmol) was added to a 100 mL 2-neck round-bottom flask equipped with a magnetic stirrer, a septum, and a pressure-equalizer dropping funnel. The flask was flushed with nitrogen through the septum. 4-Methylacetophenone (13.3 mL, 100 mmol) was added to the flask via the dropping funnel over a period of 10 min. After the mixture was stirred for additional 30 min, bromine (5.7 mL, 110 mmol) was added dropwise over a period of 5 min. The reaction was completed when the reaction mixture solidified and no more hydrogen bromide was generated. The solidified mixture was transferred portionwise to a 3N aqueous HCl solution (250 mL). The dark oil at the bottom of the solution was extracted by ether (3×30 mL). The organic layer was then washed by a saturated $NH_4Cl$ aqueous solution (50 mL), dried over with anhydrous magnesium sulfate, and concentrated to get a crude product. The crude product was further purified by distillation under reduced pressure (118° C., 3 mm Hg) to give 18.53 g (87% yield) of the desired product. m.p. 94–95° C.; $^1H$ NMR (300

MHz, CDCl$_3$) δ 2.46 (3H, s), 2.58 (3H, s), 7.33 (1H, d, J=4.7 Hz), 7.79 (1H, dd, J=4.7, 0.99 Hz), 8.12 (1H, d, J=0.99 Hz); $^{13}$C NMR (75 MHz, CDCl$_3$) δ 23.19, 26.52, 123.21, 127.08, 130.87, 132.32, 136.46, 143.53, 196.4; IR (neat) 3024 (s), 1684 (s), 1599 (m), 1383 (m), 1521 (s), 1039 (m), 958 (w), 907 (m), 831 (w) cm$^{-1}$; MS m/z 212 (M$^+$), 199, 197, 171, 169, 89; HRMS calcd.: C$_9$H$_9$OBr 211.9837, found: 211.9840.

(2) Synthesis of 1-(3-bromo-4-methyl-phenyl)ethanol

Lithium aluminum hydride (6.45 g, 170 mmol) was added to a 250 mL round-bottom flask equipped with a magnetic stirrer bar and a septum. The flask was dried under vacuum and then filled with nitrogen. Anhydrous ether (50 mL) was first injected into the flask. Subsequently, a solution of 3-bromo-4-methylacetophenone (38 g, 180 mmol) in anhydrous ether (50 mL) was injected into the flask dropwise. The reaction mixture was stirred until no more gas was generated. The mixture was poured into a dilute HCl aqueous solution (240 mL), extracted with ethyl acetate (4×30 mL), washed over a saturated NH$_4$Cl aqueous solution (50 mL), dried over anhydrous magnesium sulfate, and concentrated under vacuum to give a crude product. The crude product was further purified by distillation under reduced pressure (130° C., 4 mm Hg) to give 31.35 g (81% yield) of the desired product. $^1$H NMR (300 MHz, CDCl$_3$) δ 1.47 (3H, t, J=6.4 Hz), 1.76 (1H, s), 2.38 (3H, s), 4.84 (1H, q, J=6.4 Hz), 7.20 (2H, s), 7.55 (1H, s); $^3$C NMR (75 MHz, CDCl$_3$) δ 22.54, 25.16, 69.33, 124.30, 124.93, 129.34, 130.82, 136.88, 145.27; IR (neat) 3024 (s), 2997 (s), 2927 (m), 1605 (w), 1562 (w), 1494 (m), 1452 (m), 1381 (m), 1331 (w), 1255 (m), 1091 (m), 1038 (m), 1009 (m), 908 (m), 822 (m), 733 (s) cm$^{-1}$; MS m/z 214 (M$^+$), 199, 197, 171, 169, 119, 91; HRMS calcd for C$_9$H$_{11}$OBr 213.9993, found 213.9995.

(3) Synthesis of 3-bromo-4-methyl-styrene

KHSO$_4$ (0.55 g, 34 mmol), hydroquinone (0.142 g, 1.3 mmol), and 1-(3-bromo-4-methyl-phenyl)ethanol (17.2 g, 80 mmol) were added to a 25 mL round-bottom flask equipped with a distillation equipment. Under stirring, the system was vacuumed at 3 mm Hg and heated. A liquid product (13.6 g, 86% yield) was colleted at 102° C. (3 mm Hg). $^1$H NMR (300 MHz, CDCl$_3$) δ 2.37 (3H, s), 5.23 (1H, d, J=10.9 Hz), 5.69 (1H, d, J=17.6 Hz), 6.60 (1H, dd, J=10.9, 17.6 Hz), 7.16 (1H, d, J=7.8 Hz), 7.21 (1H, d, J=7.8 Hz), 7.57 (1H, s); $^{13}$C NMR (75 MHz, CDCl$_3$) δ 22.63, 114.32, 125.04, 125.09, 129.92, 130.76, 135.30, 137.11, 137.22 ppm; IR (neat) 3091 (m), 3063 (m), 3016 (s), 2985 (s), 2964 (m), 1899 (w), 1833 (w), 1701 (w), 1629 (m), 1602 (m), 1554 (s), 1492 (s), 1450 (s), 1380 (s), 1304 (w), 1278 (m), 1205 (m), 1037 (s), 989 (s), 914 (s), 833 (s), 854 (s), 826 (s) cm$^{-1}$; MS m/z 197(M$^+$+1) 171, 169, 117, 115, 91, 89; HRMS calcd.: C$_9$H$_9$Br 195.9888, found: 195.9887.

(4) Synthesis of 3-(diphenylphosphino)-4-methyl-styrene

Mg (0.72 g, 30 mmol) was placed in a 50 mL of round-bottom flask. The flask was dried and filled with nitrogen. Anhydrous THF (10 mL) was injected first and followed by injection of a half amount of a solution of 3-bromo-4-methyl-styrene (3.94 g, 20 mmol) in anhydrous THF (10 mL). After an exothermic reaction started, the second half of the solution was added. The resulting Grignard reagent was added to a solution of chlorodiphenylphosphine (5.25 g, 25 mmol) in anhydrous THF (10 mL) at 0° C. After the addition, the reaction mixture was warmed to the room temperature and stirred for another 20 h. Then, it was poured into a saturated NH$_4$Cl aqueous solution (10 mL) at 0° C. and extracted with anhydrous THF (3×20 mL). The organic layer was dried over anhydrous magnesium sulfate and concentrated to a volume of 5 mL. Hexane was added into the resulting oil to precipitate by-products. After filtration and concentration, the residue was purified by a flash column chromatography (hexane/EAC=4/1) to afford 2.42 g of the desired product (39% yield). $^1$H NMR (300 MHz, CDCl$_3$) δ 2.36 (3H, s), 5.06 (1H, d, J=10.9 Hz), 5.42 (1H, d, J=17.6 Hz), 6.48 (1H, q, J=10.9, 17.6 Hz), 6.79 (1H, q, J=2.1, 5.8 Hz), 7.20–7-34 (11H, m); $^{13}$C NMR (75 MHz, CDCl$_3$) δ 20.8, 21.1, 113.0, 126.2, 128.5, 128.6, 128.8, 130.2, 130.3, 130.7, 133.9, 134.1, 135.1, 136.0, 136.3, 136.5, 141.7 ppm; $^{31}$P NMR (121 MHz, CDCl$_3$) δ−12.34 ppm; IR (neat) 3057 (m), 3016 (s), 2974 (m), 1957 (w), 1900 (w), 1819 (w), 1629 (m), 1589 (m), 1479 (s), 1435 (s), 1380 (m), 1306 (w), 1262 (m), 1179 (m), 1152 (m), 1093 (m), 1028 (m), 992 (m), 911 (s), 830 (s), 699 (s); MS m/z 302 (M$^+$) 223, 183, 165, 152, 115, 78; HRMS calcd for C$_{21}$H$_{19}$P 302.1224, found 302.1227.

(5) Synthesis of trans-di(μ-acetato)-bis[3-(diphenylphosphino)-4-styryl]dipalladium(II)

Pd(OAc)$_2$ (0.225 g, 1 mmol) was solvated in anhydrous toluene (20 mL) in a 50 mL round-bottom flask. A solution of 3-(diphenylphosphino)-4-methyl-styrene (0.333 g, 1.1 mmol) in anhydrous toluene (4 mL) was injected into the flask. The reaction mixture was heated at 50° C. for 5 min, and then cooled slowly to the room temperature. The mixture was concentrated to one third of the original volume. Hexane (25 mL) was added to precipitate a crude product. The crude product was recrystallized repeatedly in toluene/hexane to afford 0.34 g of the desired product (74% yield). $^{31}$P NMR (121 MHz, CDCl$_3$) δ 19.01 ppm.

(6) Synthesis of Compound 5

Trans-di(μ-acetato)-bis[3-(diphenylphosphino)-4-styryl] dipalladium(II) (93 mg, 0.1 mmol) was added to a test tube and flushed with nitrogen. A solution of styrene (62 mg, 0.6 mmol) in benzene (2 mL) was injected into the test tube. Then, 2,2'-azobisisobutyronitrile (18 mg, 0.01 mmol) in benzene (1 mL) was injected into the test tube. After stirred at 70° C. for 40 h, the reaction mixture was concentrated to dryness. The dry solid was repeatedly washed by 1:15 THF/hexane to afford 0.11 g of the desired product (66% yield). $^{31}$P NMR (121 MHz, CDCl$_3$) δ 19.01 ppm.

EXAMPLE 2

The Heck Reaction in the Presence of Compound 5

Compound 5 (30 mg, 2 μmol Pd), iodobenzene (0.20 g, 1 mmol), methyl acrylate (0.13 g, 1.5 mmol), sodium acetate (0.12 g, 1.5 mmol), and N,N-dimethylacetamide (3 mL) were sequentially added to a 15 mL septum-sealed test tube under protection of nitrogen. The reaction mixture was heated at 100° C. for 8 h. After it was cooled to the room temperature, 8 mL of anhydrous ether was added to precipitate compound 5. The mixture was centrifuged and the upper liquid layer was transferred via a syringe into a 20 mL round-bottom flask. Repeated the above precipitation procedure once. The combined liquid layer was concentrated under reduced pressure to give an oily residue. A saturated ammonium chloride solution (5 mL) was then added. The resulting mixture was extracted by ethyl acetate (10 mL×3), dried over anhydrous magnesium sulfate, filtrated, and concentrated to give a crude product. The crude product was further purified by column chromatography (silica gel, hexane/ethyl acetate=4/1) to give 0.16 g (99% yield) of transmethyl cinnamate. $R_f$=0.53 (9:1 hexane:ethyl acetate), $^1$H NMR (300 MHz, CDCl$_3$) δ 3.81 (s, 3H), 6.45 (d, J=15.6 Hz, 1H), 7.29–7.64 (m, 5H), 7.69 (d, J=15.6 Hz, 1H) ppm.

EXAMPLE 3

The Suzuki Reaction in the Presence of Compound 5

Compound 5 (30 mg, 2 μmol Pd), 1-(4-bromophenyl)ethan-1-one (0.20 g, 1 mmol), phenylboronic acid (0.15 g, 1.2 mmol), potassium carbonate (0.21 g, 1.5 mmol), and o-xylene (3 mL) were sequentially added to a 15 mL septum-sealed test tube under protection of nitrogen. The mixture was then heated at 130° C. for 5 h. After it was cooled to the room temperature, 8 mL of anhydrous ether was added to precipitate compound 5. The mixture was centrifuged and f the upper liquid layer was transferred via a syringe into a 20 mL round-bottom flask. Repeated the above precipitation procedure once. The combined liquid layer was concentrated under reduced pressure to give an oily residue. A saturated ammonium chloride solution (5 mL) was then added. The resulting mixture was extracted by ethyl acetate (10 mL×3), dried over anhydrous magnesium sulfate, filtrated, and concentrated to give a crude product. The crude product was further purified by column chromatography (silica gel, hexane/ethyl acetate=4/1) to give 0.20 g (99% yield) of 4-acetylbiphenyl. $^1$H NMR (300 MHz, DMSO-d$_6$) δ 2.61 (s, 3H), 7.42–7.44 (m, 1H), 7.48–7.51 (m, 2H), 7.73 (d, J=8.5 Hz, 2H), 7.81 (d, J=8.5 Hz, 2H), 7.69 (d, J=8.5 Hz, 2H) ppm.

EXAMPLE 4

The Sonogashira Reaction in the Presence of Compound 5

Compound 5 (30 mg, 2 μmol Pd), 1-(4-bromo-phenyl)ethan-1-one (0.20 g, 1 mmol), phenylacetylene (0.16 g, 1.5 mmol), and triethylamine (3 mL) were sequentially added into a 15 mL septum-sealed test tube under protection of nitrogen. The mixture was then heated at 90° C. for 72 h. After it was cooled to the room temperature, 8 mL of anhydrous ether was added to precipitate compound 5. The mixture was centrifuged and the upper liquid layer was transferred via a syringe into a 20 mL round-bottom flask. Repeated the above precipitation procedure once. The combined liquid layer was concentrated under reduced pressure to give an oily residue. A saturated ammonium chloride solution (5 mL) was then added. The resulting mixture was extracted by ethyl acetate (10 mL×3), dried over anhydrous magnesium sulfate, filtrated, and concentrated to give a crude product. The crude product was further purified by column chromatography (silica gel, hexane/ethyl acetate=4/1) to give 0.21 g (98% yield) of 1-(4-acetylphenyl)-2-phenylethyne. $^1$H NMR (400 MHz, CDCl$_3$) δ 2.57 (s, 3H), 7.33–7.35 (m, 3H), 7.52–7.54 (m, 2H), 7.58 (d, J=8.2 Hz, 2H), 7.91 (d, J=8.2 Hz, 2H) ppm.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the above-described palladacycle catalysts also can be made, tested for the above-described activities and used to practice this invention. Thus, other embodiments are also within the claims.

What is claimed is:

1. A palladacycle catalyst of formula (I)

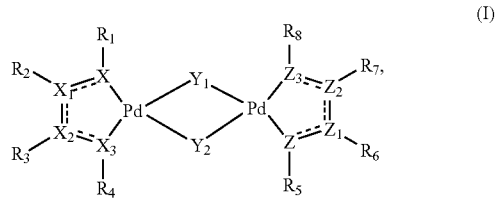

in which each ⎓ is a single bond or a double bond, provided that if one ⎓ is a double bond, its neighboring ⎓ is not a double bond;

each of X and Z, independently, is —P(R')—, —S—, —N(R')—, or —N=, in which R' is alkyl, aryl, cyclyl, heteroaryl, or heterocyclyl;

each of $Y_1$ and $Y_2$, independently, is an anion of an organic or inorganic acid;

each of $X_1$, $X_2$, $X_3$, $Z_1$, $Z_2$, and $Z_3$, independently, is —C=, —CR''—, in which R'' is H, alkyl, aryl, cyclyl, heteroaryl, or heterocyclyl; and each of $R_1$, $R_2$, $R_3$, $R_4$, $R_5$, $R_6$, $R_7$, and $R_8$, independently, is H, alkyl, aryl, cyclyl, heteroaryl, or heterocyclyl, or $R_1$, X, $X_1$, and $R_2$, together form a 3–8 membered ring, or $R_2$, $X_1$, $X_2$, and $R_3$, together form a 3–8 membered ring, or $R_3$, $X_2$, $X_3$, and $R_4$, together form a 3–8 membered ring, or $R_5$, Z, $Z_1$, and $R_6$, together form a 3–8 membered ring, or $R_6$, $Z_1$, $Z_2$, and $R_7$, together form a 3–8 membered ring, or $R_7$, $Z_2$, $Z_3$, and $R_8$, together form a 3–8 membered ring; wherein at least one of $R_1$, $R_2$, $R_3$, $R_4$, $R_5$, $R_6$, $R_7$, and $R_8$, or the ring formed from $R_1$, X, $X_1$, and $R_2$, or the ring formed from $R_2$, $X_1$, $X_2$, and $R_3$, or the ring formed from $R_3$, $X_2$, $X_3$, and $R_4$, or the ring formed from $R_5$, Z, $Z_1$, and $R_6$, or the ring formed from $R_6$, $Z_1$, $Z_2$, and $R_7$, or the ring formed from $R_7$, $Z_2$, $Z_3$, and $R_8$ is connected to a first polymer.

2. The catalyst of claim 1, wherein each of X and Z is —N=.

3. The catalyst of claim 2, wherein $Y_1$ and $Y_2$ are identical.

4. The catalyst of claim 1, wherein each of X and Z is —S—.

5. The catalyst of claim 4, wherein $Y_1$ and $Y_2$ are identical.

6. The catalyst of claim 1, wherein X is —P(R')—.

7. The catalyst of claim 6, wherein $X_1$ is —C=, $X_2$ is —C=, $X_3$ is —CR''—, the bond between X and $X_1$ is a single bond, the bond between $X_1$ and $X_2$ is a double bond, and the bond between $X_2$ and $X_3$ is a single bond.

8. The catalyst of claim 7, wherein Z is —P(R')—.

9. The catalyst of claim 8, wherein $Z_1$ is —C=, $Z_2$ is —C=, $Z_3$ is —CR''—, the bond between Z and $Z_1$ is a single bond, the bond between $Z_1$ and $Z_2$ is a double bond, and the bond between $Z_2$ and $Z_3$ is a single bond.

10. The catalyst of claim 9, wherein $R_2$, $X_1$, $X_2$, and $R_3$ together form phenyl.

11. The catalyst of claim 10, wherein the first polymer is connected to the phenyl formed from $R_2$, $X_1$, $X_2$, and $R_3$ by a covalent bond.

12. The catalyst of claim 11, wherein the first polymer is polystyrene.

13. The catalyst of claim 12, wherein $R_6$, $Z_1$, $Z_2$, and $R_7$ together form phenyl.

14. The catalyst of claim 13, wherein a second polymer is connected to phenyl formed from $R_6$, $Z_1$, $Z_2$, and $R_7$ by a covalent bond.

15. The catalyst of claim 14, wherein each of the first and second polymers is polystyrene.

16. The catalyst of claim 15, wherein each of $Y_1$ and $Y_2$ is $CH_3C(O)O^-$.

17. The catalyst of claim 1, wherein the catalyst is

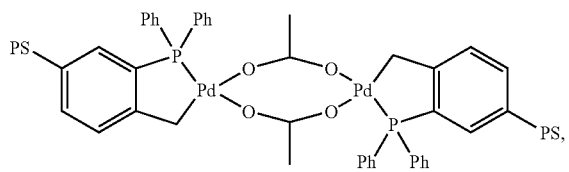

in which PS is polystyrene having a degree of polymerization of 6.

18. A method for promoting a coupling reaction, comprising conducting the reaction in the presence of a palladacycle catalyst of formula (I)

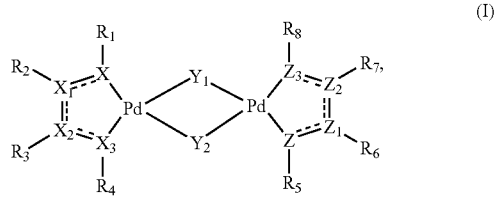

in which
each $=\!=\!=$ is a single bond or a double bond, provided that if one $=\!=\!=$ is a double bond, its neighboring $=\!=\!=$ is not a double bond;
each of X and Z, independently, is —P(R')—, —S—, —N(R')—, or —N═, in which R' is alkyl, aryl, cyclyl, heteroaryl, or heterocyclyl;
each of $Y_1$ and $Y_2$, independently, is an anion of an organic or inorganic acid;
each of $X_1$, $X_2$, $X_3$, $Z_1$, $Z_2$, and $Z_3$, independently, is —C═, —CR"—, in which R" is H, alkyl, aryl, cyclyl, heteroaryl, or heterocyclyl; and
each of $R_1$, $R_2$, $R_3$, $R_4$, $R_5$, $R_6$, $R_7$, and $R_8$, independently, is H, alkyl, aryl, cyclyl, heteroaryl, or heterocyclyl, or X, $R_1$, $R_2$, and $X_1$ together form a 3–8 membered ring, or $X_1$, $R_2$, $R_3$, and $X_2$ together form a 3–8 membered ring, or $X_2$, $R_3$, $R_4$, and $X_3$ together form a 3–8 membered ring, or Z, $R_5$, $R_6$, and $Z_1$ together form a 3–8 membered ring, or $Z_1$, $R_6$, $R_7$, and $Z_2$ together form a 3–8 membered ring, or $Z_2$, $R_7$, $R_8$, and $Z_3$ together form a 3–8 membered ring; wherein at least one of $R_1$, $R_2$, $R_3$, $R_4$, $R_5$, $R_6$, $R_7$, and $R_8$, or the ring formed from $R_1$, X, $X_1$, and $R_2$, or the ring formed from $R_2$, $X_1$, $X_2$, and $R_3$, or the ring formed from $R_3$, $X_2$, $X_3$, and $R_4$, or the ring formed from $R_5$, Z, $Z_1$, and $R_6$, or the ring formed from $R_6$, $Z_1$, $Z_2$, and $R_7$, or the ring formed from $R_7$, $Z_2$, $Z_3$, and $R_8$ being connected to a first polymer.

19. The method of claim 18, wherein each of X and Z is —N═.

20. The method of claim 19, wherein $Y_1$ and $Y_2$ are identical.

21. The method of claim 18, wherein each of X and Z is —S—.

22. The method of claim 21, wherein $Y_1$ and $Y_2$ are identical.

23. The method of claim 22, wherein X is —P(R')—, $X_1$ is —C═, $X_2$ is —C═, $X_3$ is —CR"—, the bond between X and $X_1$ is a single bond, the bond between $X_1$ and $X_2$ is a double bond, and the bond between $X_2$ and $X_3$ is a single bond.

24. The method of claim 23, wherein Z is —P(R')—, $Z_1$ is —C═, $Z_2$ is —C═, $Z_3$ is —CR"—, the bond between Z and $Z_1$ is a single bond, the bond between $Z_1$ and $Z_2$ is a double bond, and the bond between $Z_2$ and $Z_3$ is a single bond.

25. The method of claim 24, wherein $X_1$, $R_1$, $R_2$, and $X_2$ together form phenyl.

26. The method of claim 25, wherein the first polymer is connected to phenyl formed from $R_2$, $X_1$, $X_2$, and $R_3$ by a covalent bond.

27. The method of claim 26, wherein $R_6$, $Z_1$, $Z_2$, and $R_7$ together form phenyl.

28. The method of claim 27, wherein the second polymer is connected to phenyl formed from $R_6$, $Z_1$, $Z_2$, and $R_7$ by a covalent bond.

29. The method of claim 28, wherein each of the first and second polymers is polystyrene.

30. The method of claim 29, wherein each of $Y_1$ and $Y_2$ is $CH_3C(O)O^-$.

31. The method of claim 18, wherein the catalyst is

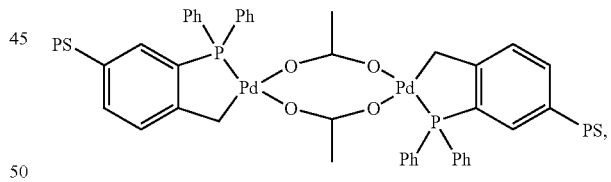

in which PS is polystyrene having a degree of polymerization of 6.

32. A method for preparing a palladacycle catalyst of formula (I)

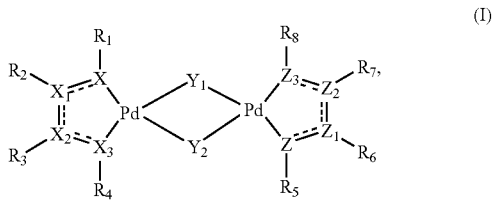

in which
  each ⚌ is a single bond or a double bond, provided that if one ⚌ is a double bond, its neighboring ⚌ is not a double bond;
  each of X and Z, independently, is —P(R')—, —S—, —N(R')—, or —N═, in which R' is alkyl, aryl, cyclyl, heteroaryl, or heterocyclyl;
  each of $Y_1$ and $Y_2$ is an anion of an organic or inorganic acid;
  each of $X_1$, $X_2$, $X_3$, $Z_1$, $Z_2$, and $Z_3$, independently, is —C═, —CR"—, in which R" is H, alkyl, aryl, cyclyl, heteroaryl, or heterocyclyl; and
  each of $R_1$, $R_2$, $R_3$, $R_4$, $R_5$, $R_6$, $R_7$, and $R_8$, independently, is H, alkyl, aryl, cyclyl, heteroaryl, or heterocyclyl, or X, $R_1$, $R_2$, and $X_1$ together form a 3–8 membered ring, or $X_1$, $R_2$, $R_3$, and $X_2$ together form a 3–8 membered ring, or $X_2$, $R_3$, $R_4$, and $X_3$ together form a 3–8 membered ring, or Z, $R_5$, $R_6$, and $Z_1$ together form a 3–8 membered ring, or $Z_1$, $R_6$, $R_7$, and $Z_2$ together form a 3–8 membered ring, or $Z_2$, $R_7$, $R_8$, and $Z_3$ together form a 3–8 membered ring; wherein at least one of $R_1$, $R_2$, $R_3$, $R_4$, $R_5$, $R_6$, $R_7$, and $R_8$, or the ring formed from $R_1$, X, $X_1$, and $R_2$, or the ring formed from $R_2$, $X_1$, $X_2$, and $R_3$, or the ring formed from $R_3$, $X_2$, $X_3$, and $R_4$, or the ring formed from $R_5$, Z, $Z_1$, and $R_6$, or the ring formed from $R_6$, $Z_1$, $Z_2$, and $R_7$, or the ring formed from $R_7$, $Z_2$, $Z_3$, and $R_8$ is connected to first polystyrene;
  the method comprising reacting styrene with a palladacycle compound of formula (I), in which
  each ⚌ is a single bond or a double bond, provided that if one ⚌ is a double bond, its neighboring ⚌ is not a double bond;
  each of X and Z, independently, is —P(R')—, —S—, —N(R')—, or —N═, in which R' is alkyl, aryl, cyclyl, heteroaryl, or heterocyclyl;
  each of $Y_1$ and $Y_2$ is an anion of an organic or inorganic acid;
  each of $X_1$, $X_2$, $X_3$, $Z_1$, $Z_2$, and $Z_3$, independently, is —C═, —CR"—, in which R" is H, alkyl, aryl, cyclyl, heteroaryl, or heterocyclyl; and
each of $R_1$, $R_2$, $R_3$, $R_4$, $R_5$, $R_6$, $R_7$, and $R_8$, independently, is H, alkyl, aryl, cyclyl, heteroaryl, or heterocyclyl, or X, $R_1$, $R_2$, and $X_1$ together form a 3–8 membered ring, or $X_1$, $R_2$, $R_3$, and $X_2$ together form a 3–8 membered ring, or $X_2$, $R_3$, $R_4$, and $X_3$ together form a 3–8 membered ring, or Z, $R_5$, $R_6$, and $Z_1$ together form a 3–8 membered ring, or $Z_1$, $R_6$, $R_7$, and $Z_2$ together form a 3–8 membered ring, or $Z_2$, $R_7$, $R_8$, and $Z_3$ together form a 3–8 membered ring; wherein one of $R_1$, $R_2$, $R_3$, $R_4$, $R_5$, $R_6$, $R_7$, and $R_8$, or the ring formed from $R_1$, X, $X_1$, and $R_2$, or the ring formed from $R_2$, $X_1$, $X_2$, and $R_3$, or the ring formed from $R_3$, $X_2$, $X_3$, and $R_4$, or the ring formed from $R_5$, Z, $Z_1$, and $R_6$, or the ring formed from $R_6$, $Z_1$, $Z_2$, and $R_7$, or the ring formed from $R_7$, $Z_2$, $Z_3$, and $R_8$ is connected to a first vinyl group.

33. The method of claim 32, wherein the palladacycle catalyst of formula (I) further has second polystyrene, which is connected to one of $R_1$, $R_2$, $R_3$, $R_4$, $R_5$, $R_6$, $R_7$, and $R_8$, or the ring formed from X, $R_1$, $R_2$, and $X_1$, or the ring formed from $X_1$, $R_2$, $R_3$, and $X_2$, or the ring formed from $X_2$, $R_3$, $R_4$, and $X_3$, or the ring formed from Z, $R_5$, $R_6$, and $Z_1$, or the ring formed from $Z_1$, $R_6$, $R_7$, and $Z_2$, or the ring formed from $Z_2$, $R_7$, $R_8$, and $Z_3$; and the palladacycle compound further has a second vinyl group, which is connected to one of $R_1$, $R_2$, $R_3$, $R_4$, $R_5$, $R_6$, $R_7$, and $R_8$, or the ring formed from X, $R_1$, $R_2$, and $X_1$, or the ring formed from $X_1$, $R_2$, $R_3$, and $X_2$, or the ring formed from $X_2$, $R_3$, $R_4$, and $X_3$, or the ring formed from Z, $R_5$, $R_6$, and $Z_1$, or the ring formed from $Z_1$, $R_6$, $R_7$, and $Z_2$, or the ring formed from $Z_2$, $R_7$, $R_8$, and $Z_3$.

34. The method of claim 33, wherein the catalyst is

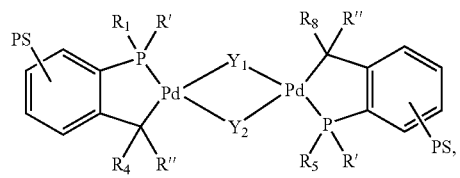

in which each of $R_1$, R', $R_4$, R", $R_5$, and $R_8$, independently, is H, alkyl, aryl, cyclyl, heteroaryl, or heterocyclyl;
$Y_1$ and $Y_2$ are identical; and PS is polystyrene; and
the palladacycle compound is

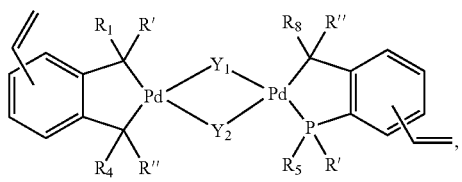

in which each of each of $R_1$, R', $R_4$, R", $R_4$, and $R_8$, independently, is H, alkyl, aryl, cyclyl, heteroaryl, or heterocyclyl; and $Y_1$ and $Y_2$ are identical.

35. The method of claim 34, wherein the catalyst is

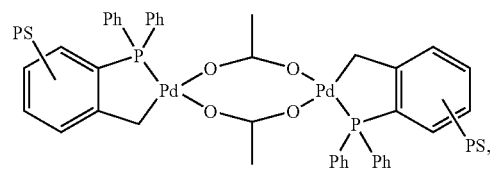

in which
  PS is polystyrene having a degree of polymerization of 6; and
the palladacycle compound is

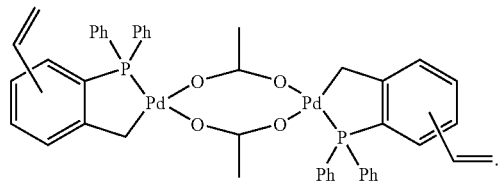

* * * * *